United States Patent
Berti

(10) Patent No.: US 8,352,073 B2
(45) Date of Patent: Jan. 8, 2013

(54) MOBILE DEVICE FOR IRRADIATION AND DETECTION OF RADIATION

(76) Inventor: Giovanni Berti, Pisa (IT)

(*) Notice: Subject to any disclaimer, the term of this patent is extended or adjusted under 35 U.S.C. 154(b) by 833 days.

(21) Appl. No.: 11/922,842

(22) PCT Filed: Jun. 20, 2006

(86) PCT No.: PCT/EP2006/063324
§ 371 (c)(1),
(2), (4) Date: Feb. 3, 2009

(87) PCT Pub. No.: WO2006/136542
PCT Pub. Date: Dec. 28, 2006

(65) Prior Publication Data
US 2009/0216373 A1  Aug. 27, 2009

(30) Foreign Application Priority Data

Jun. 20, 2005 (IT) .................. FI2005A0137

(51) Int. Cl.
*G05B 15/00* (2006.01)
*G21K 1/00* (2006.01)
*G05B 19/19* (2006.01)
*G01N 23/20* (2006.01)

(52) U.S. Cl. ............ 700/248; 700/245; 700/258; 901/2; 901/15; 901/28

(58) Field of Classification Search .......... 700/245–264; 378/79, 81; 901/1–50
See application file for complete search history.

(56) References Cited

U.S. PATENT DOCUMENTS

| | | | |
|---|---|---|---|
| 4,644,761 A * | 2/1987 | Chatzipetros et al. | 62/51.1 |
| 4,972,448 A * | 11/1990 | Munekawa | 378/81 |
| 5,359,640 A | 10/1994 | Fink et al. | |
| 5,602,889 A | 2/1997 | Oldendorf et al. | |
| 6,064,717 A | 5/2000 | Ortega et al. | |
| 6,678,347 B1 * | 1/2004 | Kozaczek et al. | 378/75 |
| 7,258,485 B2 * | 8/2007 | Nakano et al. | 378/205 |
| 2003/0012334 A1 * | 1/2003 | Kurtz et al. | 378/73 |
| 2003/0219099 A1 * | 11/2003 | He et al. | 378/70 |
| 2006/0023222 A1 * | 2/2006 | Binder et al. | 356/446 |

FOREIGN PATENT DOCUMENTS

| | | |
|---|---|---|
| EP | 0 291 320 A1 | 11/1988 |
| EP | 0 512 620 A2 | 11/1992 |
| WO | WO 03/060498 A1 | 7/2003 |
| WO | WO 2006003430 A1 * | 1/2006 |
| WO | WO 2006/042211 A2 | 4/2006 |
| WO | WO 2006/042569 A1 | 4/2006 |

OTHER PUBLICATIONS

Jiang, "A Review of Recent Developments in Robot Metrology," Journal of Manufacturing Systems 7, No. 4, 1988, pp. 339-357.
International Search Report, Dec. 7, 2006.

* cited by examiner

*Primary Examiner* — Khoi Tran
*Assistant Examiner* — Dale Moyer
(74) *Attorney, Agent, or Firm* — Abelman, Frayne & Schwab

(57) ABSTRACT

A mobile equipment endowed with a neutrons source possibly in combination with other radiation sources including a robot system that, moving on a controlled trajectory, realize the conditions to observe from different positions the radiation emerging from a specimen either mobile or fixed, properly irradiated, is described.

15 Claims, 4 Drawing Sheets

Figure 1 (a)
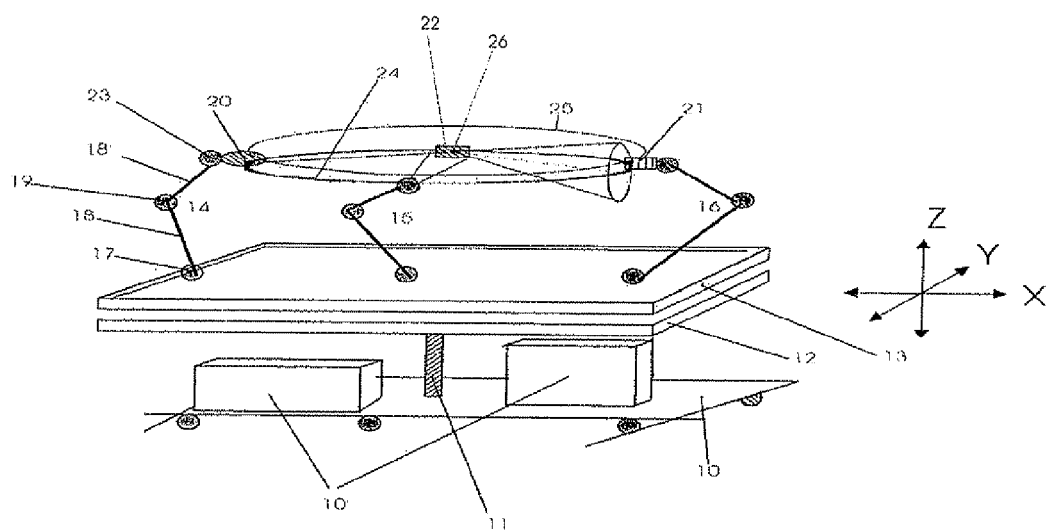
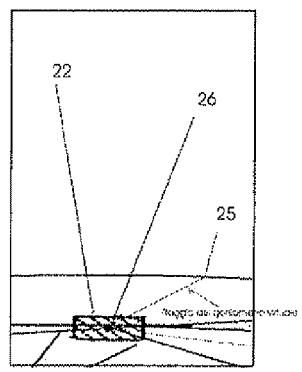
Figure 1 (b)

MOBILE DEVICE FOR IRRADIATION AND DETECTION OF RADIATION

FIELD OF THE INVENTION

The present invention refers to the field of mobile devices for irradiation and detection of radiation in destructive and non destructive integrated controls.

STATE OF THE ART

The devices for irradiation and detection of radiation are provided with source and detector. The irradiation sources are able to emit particles (or waves) of different nature (x ray, neutrons electrons, ultrasounds and so on). Normally no more then one source is used contemporaneously or interchangeably on the same instrumentation. Moreover, these devices present problems when they must be moved form one place to another, problems mainly connected to the size of the equipment itself and of its auxiliary devices (e.g. high voltage generators, cooled fluids containers, confinement containers). For example, when using neutrons source for diffraction purposes, generally the instruments are installed in labs where nuclear reactors with high neutron flux are present or where neutrons are provided by a collision process in accelerating machines so providing the suitable neutrons flux required for the diffraction measurement. Therefore such kind of instruments are very big and heavy thus making them installable only in large laboratory premises. Similar problems exist when using electron sources, because even in this case the dimensions required prevent an easy deplacement of the device.

Since any kind of radiation has a characteristic impact on the material of the component under investigation, analyses carried on using different kind of sources give generally information that are mutually complementary.

SUMMARY OF THE INVENTION

From what said above, it is evident the importance of a device endowed of good flexibility and offering the availability to implement investigation everywhere it's necessary and whatever irradiating source is requested.

Since many analyses have a relative nature; i.e. they are implemented in relation to other reference measures and reference specimen, it is necessary to give the preferred scheme to whom the present invention is referred.

Therefore, according to a preferred application, the invention is connected with neutron diffraction, and the geometrical rules to obtain diffraction are taken in special consideration in the present description independently form the kind of radiation used (neutrons, electrons, X-rays, etc).

Up to now, the size of the radiation thermalizers and of the confining systems has prevented the realization of neutrons diffractometers with devices and controllers suitable for movement and transportation of the full instrumentation.

One of the innovative aspects described here is the combination between the refraction effect (used to thermalize the neutrons) and the total reflection effect.

Other aspects come from using combined irradiation sources with different nature and the possibility of controlling the movement of the devices on path that permit to obtain advantageously measures useful for diagnosis and therapy.

BRIEF DESCRIPTION OF THE FIGURES

FIG. 1(a) shows a schematic view of the robotic functioning of the device according to the invention;

FIG. 1(b) shows a particular detail of FIG. 1(a).

DETAILED DESCRIPTION OF THE INVENTION

Figure 2:
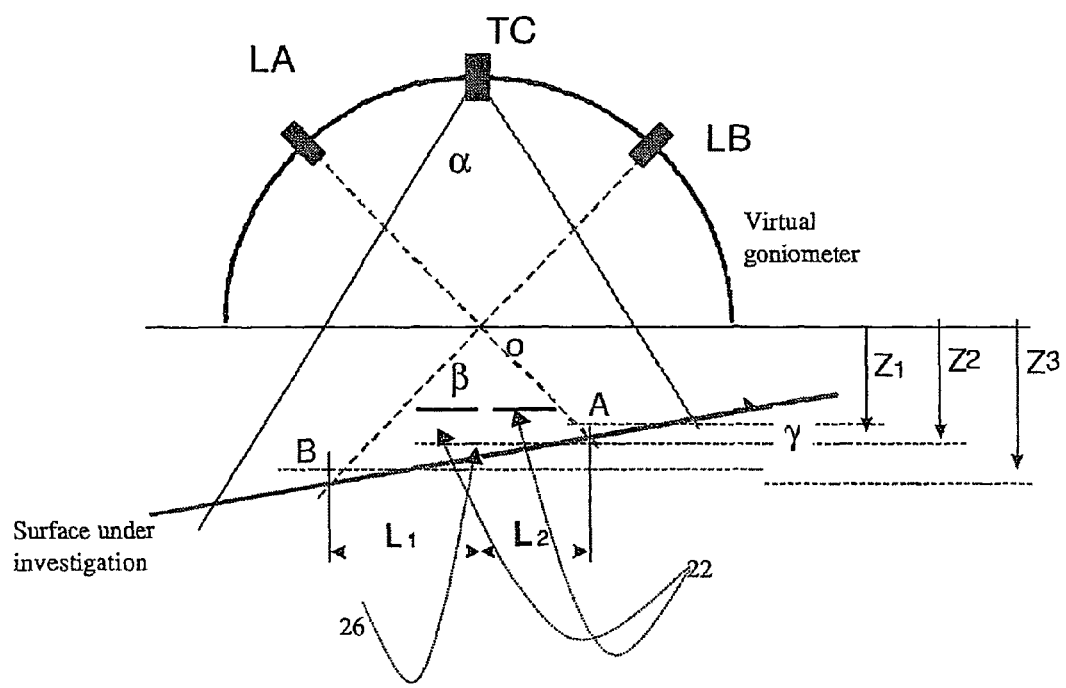
FIG. 2 shows the mutual positioning of the pointing system components.

It is described a mobile or transportable device with a neutrons source eventually in combination with sources of other radiations. This device comprises a robotic system that affords to observe the radiation emerging from a specimen under various angles thanks to the fact that the robots are moving on controlled path.

As said above, since the diffraction of neutrons radiation beam emerging from specimen is the preferred application of the invention, this is described in major details.

The neutrons diffraction in fact requires the realization of conditions more binding compared to others types of methods and includes the use of converging and thermalizing systems that are not compulsory for other type of analysis.

Detailed Description of the Invention

The present invention makes available a device, eventually a multifunction device, that allows to use radiations of different nature for different or complementary purposes (diagnosis, therapy, repair, branding, etc.), thanks to the invention device it is possible to perform the requested operations wherever it is requested and even on parts of plants in exercise. It works preferably as a diffractometer because of the presence of robots that moving along controlled paths substitute the traditional mechanic goniometer used by lab diffractometers. This robotic system and the related movement allows to realize an instrumental configuration that is defined "virtual goniometer configuration".

The Virtual Goniometer

FIG. 1 shows the mobile device according to the invention that comprises a mobile surface 10 on which the systems service 10' (e.g. the cooled fluid container or generator, the high voltage generators, battery, etc.) are fixed. Said surface is linked through a central shaft 11 to a shelf 12, on which a second shelf 13 is settled. This shelf 13 is capable to move respect to the shelf 12 sliding along the direction of the Cartesian axes x and y, as indicated in the figure, through mechanical gears and manually or electrically controlled guides. Even the shaft 11 is moved mechanically or manually or electrically; said shaft 11 is able to raise and fall the shelf 12.

Three Robots 14, 15 and 16 are placed on shelf 13. They can be moved along a controlled paths, thus realizing the virtual goniometer and eliminate the mechanical goniometer generally used in these kind of devices.

Each of these robots 14, 15 and 16 consists of a base 17 and two arms 18 and 18' linked between them through a joint 19 able to rotate the arm 18' respect to the arm 18.

The bases 17 of the robots 14, 15 and 16 can be provided of a trolley capable of freely moving on the shelf 13 and electrically controlled, or can slid on suitable guides obtained in the surface of the same shelf 13 itself.

The bases 17 of each robot are provided with motors able to rotate the arm 18 around the axis x and y, moreover also the joint 19 is provide of motors capable of allowing the rotation the axis y and z.

At the end of the arm 18', opposite to the one linked to the joint 19, of the two external robots 14, 16 are fixed respectively the radiation source 20 and the detector 21, while at the same extremity of the central robot 15 is fixed the pointing system with the centring window 22.

The centring window can be provided or not with a telescopic arm in order to be approached to the surface to be investigated without touching it and can be equipped with geometrical references (i.e. lines, marking, frames etc.) for the accurate positioning of the instrument respect to said surface. This window can be possibly provided with a suitable covering material to reveal the radiation (e.g. fluorescence material) and can also be equipped with means to project and detect at distance lines, masks, frames and means for sputtering covering materials.

The centring window 22 is set in a central position in respect to the source 20 and the detector 21. At the interior of the centring window 22 can be identified the centre 26 of a circle that defines the "virtual goniometer" and that contains on its circumference 25 the source 20 and the detector 21, as illustratively shown in FIG. 1b.

If preferred, also said source 20, detector 21 and the centring window 22, can be linked to the arm 18' through a joint 23 able to rotate those devices around one ore more axes x,y,z. in this way the radium of the virtual goniometer centre can be modified during a measure.

Obviously the apparatus will be also equipped with a control unit, possibly computerised, in order to control and guide all the necessary movements of the various parts forming the device as above described.

The use of parallel beams obtained through polycapillaries or graduated curve reflectors or similar devices can permit to greatly refine the measures, said devices are not compulsory but can be advantageous to increase the density of radiation on the specimen.

The Virtual Goniometer in Diffractometer Configuration

According to the preferred invention scheme, it is described the working operations of a diffractometer with virtual goniometer that requires more strict constraints respect to other equipment.

In traditional lab diffractometers, or even on the movable ones that are based on one or more Euleur cradles, the elements that constitute the goniometer are mechanically defined. In this case of absence of mechanic goniometer requires the definition of geometrical figures that realize the condition of Bragg diffraction (2d sen θ=γ, where d is the lattice spacing, θ (theta) is the observation angle of the diffraction line, γ (gamma) is the wavelength of the radiation) and the suitable diffractometric geometries to measure the materials composition (mineralogical phases, chemical compounds, organic or inorganic etc.) and/or their physics and mechanical properties (residual stress, texture, micro deformation and so on).

Said geometrical figures are the centre, the radius and the circumference of the virtual goniometer, that, unlike the traditional ones for lab or movable, are not fix but variable in length.

Other geometric figures as the radius, centre, circumference of the focusing circle, diffraction planes and axes and other linked to them follow the well-known diffractometry scheme.

The Pointing and Observation System

With reference to FIG. 2, the pointing system includes preferably two optical laser LA and LB, a camera CCD (TC) and the centring window 22 confined into the opening a of the camera with the centre 26 confined in the window and virtually placed on the surface under investigation.

The pointing and observation system allows the operator to observe the environment where the instrument is working from the point of view of the end-effector of the robots. This is a valid help during the phase of manual matching of the instrument to the analysed area.

By analysing the image of the surface placed in front of the end-effector, it is possible to individuate the investigation axis, the centre of the virtual goniometer and the axial plane. Moreover it is possible to define the distance of the source from said centre and the direction of the irradiation respect to the investigation axis. It is also possible to identify the equatorial plane on which the virtual goniometer and the focusing circle are defined; consequently, it is possible to identify the paths the single parts of the device have to cover. In FIG. 2 it is shown schematically the position of the camera TC and laser LA, LB, their incident angle β (beta) in the point where the specimen has to be analysed; in general the specimen surface will be inclined of an angle γ (gamma) respect to the axis of the camera. The inclination of the laser is based on a value Z=0 when the two lasers match with the centre 26.

Using trigonometric considerations it is possible to evaluate the distances $Z_1$, $Z_2$ and $Z_3$ from the centre of the goniometer 26 of a plane perpendicular to the axis of the camera passing from the point of incidence of a laser beam with the surface to be examined and it is possible to evaluate the distances $L_1$ and $L_2$ on the surface itself. According to these evaluations it is possible to repositioning the measurement devices respect to other elements of the virtual goniometer described above.

Use of the Virtual Goniometer Diffractometer

The base 17 of the central robot 15, is the origin of the coordinate system that has to be adopted for the use of the virtual goniometer diffractometer.

The movements of the robot's 15 base and of the connected arms permit to find the position of the area that has to be investigated and its co-ordinates are calculated with reference to the origin of the system as above defined.

The area isolated by the centring window is considered a portion of the plane tangent to the focusing circle and belongs to the surface to be investigated. The centre 26 is also a point on the axis perpendicular to the equatorial plane.

Moving the base of the robot 14, that carries the source and the relatives arms, it's possible to set the robot in the appropriate asset as "source point" with the appropriate take off angle, this asset provides a direction at angle of the incident beam to said tangent plane on the point 26 of the equatorial plane (i.e. the goniometer centre). The line including the source and the point 26 lies on the equatorial plane.

Moving the base of the robot that carries the detector and the relative arms it's possible to set the robot in such a way that:

the detection point (corresponding to the detector 21) is coplanar to the source and the centre 26;

the centre 26 (identify by the centring window 22) is equidistant to the other two points; this requisite is compulsory only in the case of divergent beams (incident or diffracted). In case of parallel beams this constraint of equidistance has a minor relevance.

the alignment of the detection point and the re (as above described) forms an angle 2θ (2 theta) respect to the alignment of the source and the centre 26.

Robot 16 which carries the detector, and the robot 14 which carries the radiation source, shall be moved accordingly to what above mentioned. In the realization of a diffractometer the relative position of the robots 14, 15 and 16 shall conserve the conditions provided for the Bragg law (2d sen θ=nγ) as above defined.

This is obtained moving the two robots 14 and 16 in opposite directions respect to the investigation axis and managing that the axis of the incident beam (collimation axis) and the axis of the diffraction beam (receiving axis) lie in the same equatorial plane and form opposite angles to the vertex with the axis in the equatorial plane and orthogonal to the goniometer axis. (configuration θ: θ). When possible, the source can be kept fix and the centre 26 is moved around the goniometer axis of an angle θ/2. In this way the configuration θ: 2θ is obtained.

For alignment verification and calibration purposes, the angle θ (theta) is chosen to record a reflection compatible with the characteristics of the material and the radiation used.

Once reached the goniometric asset, a fine adjustment shall be performed in order to reach the maximum irradiation flux collected by the detector. At this point, the measure operation starts by keeping fix the robot that carries the source and the central robot (that carries the centring window) and by moving the robot that carries the detector both on the goniometric circle and on the circumference of the cone (Debije circle).

The Source

The radiation source 20 can be a particles source possibly in combination with other electromagnetic radiations sources (for examples X rays for diffraction use or spectroscopy, fluorescence, and so on) and others.

According to the invention the source is, preferably, a neutron source possibly thermalized or partially thermalized, provided with an electronic filter that cuts the neutrons with extreme energy values and convergent irradiating lenses that increase the beam density on the irradiated area unit.

Preferably, according to the invention, the neutrons are generated from a generator of little particles that striking a Deuterium target trigger the reaction $D+D\rightarrow{}^3He+n$ emitting a radiation of neutrons with appropriate energy, flux and impulse duration.

As an example the following characteristics can be considered:

Neutron energy: 2 MeV

Neutron flux included between $10^8$-$10^9$ n/s.

Duration of the impulse superior to 10 μsec and adjustable according to the source type.

According to an embodiment of the invention a pulsed source in combinations with converging lenses for neutrons is preferred.

When using a pulsed source, the duration of the impulse of the electronic filtering shall be adjusted on the characteristics of the pulsation frequencies. The energy reduction (e.g. thermalization to values of 0.025 eV) adapts the neutron beam to said diagnosis and therapeutic purposes.

The Neutrons Convergent Lenses

According to the preferred scheme of the invention, the thermalization can be properly obtained by channelling the neutrons emitted from the source towards the extraction channel through a combined process of Total Reflection and Refraction. The combination of this two effects permits to obtain a beam of parallel and thermal neutrons with a satisfactory flux and sufficient for the purpose of the equipment.

The neutrons refraction phenomenon is known since the time of the studies by C. S Schneider (Nobel prize 1994) and recently measured through the technique said "spi-echo small-angle neutron scattering". In a mono directional beam the flux is the number of neutrons that cross the surface unit orthogonal to their movement.

Through Monte Carlo simulation is possible to obtain an estimation of the neutrons emerging from a channel filled with refracting material as deuterium, water, plexiglas, polytene and so on, possibly with the addition of metal foils, in order to deviate and/or absorb the residual fast and/or epithermical neutrons.

It's possible to obtain a combination of refracting and reflecting elements that, properly fitted, allow a flux suitable for the purpose of the equipment.

Figure 3:
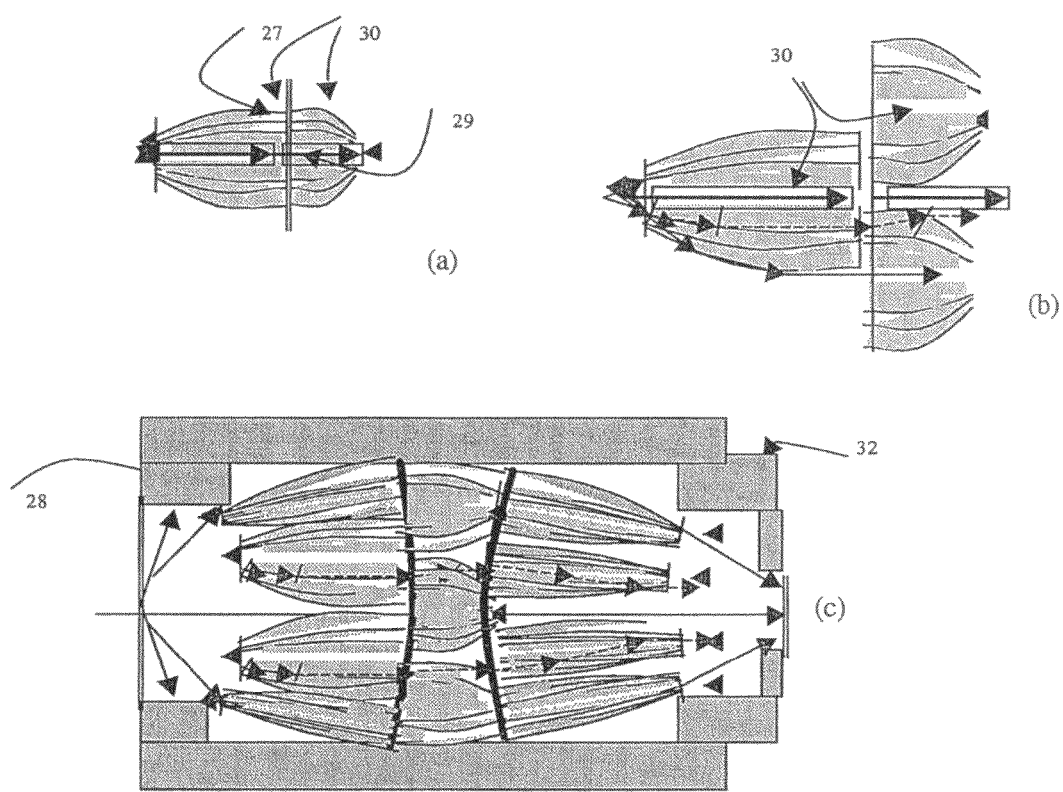
FIG. 3 shows particular details of the irradiation and thermalization converging lenses.

The FIG. 3(a) shows a scheme of the invention where the refraction effect (used to thermalize the neutrons) is coupled with the known total reflection effect and allows to build a device with convergent lens (called ToReRe lens).

Said lens comprises: channels 27 constituted by capillaries or polycapillaries fibre or multilayers planars suitably coupled and a main channel 28 that can be a glass tube, eventually shaped in the longitudinal section as a bottonhole with appropriate dimensions and size (e.g. 2 cm width on average and modulated on the longitudinal section for a length of 20 cm). Such a tube can be filled with refracting material for neutrons (e.g. $D_2O$, $H_2O$). Said channels 27 can be bent according to a graded curvature radius. Said curvature radius increases gradually with the distance of channel 27 from the axis of the lens (or central channel) 28. Each of this channels can be filled with material having increasing refraction index in order to improve the deviation effect. When said lens is coupled with an equivalent device, an extraction channel 29 can be obtained and two sectors 30 of the lens are created.

If necessary the channels of said lens contained in the two different sectors 30 can have a different curvatures and be filled with materials with different refraction index to increase the combined effect of the total reflection and refraction.

FIG. 3(b) shows an "out of phase" coupling of ToReRe lenses and constitutes a mosaic of "graded convergence" lenses.

Depending on the application, the assembling of sectors 30 can be extended to realize moderators with cubic, conical, prismatic shape, or others, as in FIG. 3(c).

This coupling has to improve the multiple deviation as a consequence of the refraction at every interface when the neutron motion direction makes it to escape from one channel to the next one. These refraction at interface favours an ondulating motion of neutrons increasing their channeling to the extraction channel.

In practice the lens has to be built taking into consideration the two different conditions that can occur:

a) the neutron has a motion direction contained into the capture angle of the central channel, but its energy has to be reduced (thermalization).

b) the neutron has a direction that cannot be confined in the central channel. Said neutron has to be thermalized in a different direction from the original one. Said neutron comes out from the central channel and meets channels containing materials with increasing refraction index. The elements contained in said materials shall have a suitable density capable of deviating gradually the motion direction as a consequence of the refraction effect (see the direction of the arrows in FIG. 3(b)). The variation of the refraction indexes of the materials met by the neutron in its paths through the channels induces little deviation that favour the ondulation to find the appropriate direction for total reflection conditions. The induced ondulations in the neutron motion and the mosaic arrangement of the different channels in different sectors favour the channelling of neutrons towards the extraction channel through the combination of multiple refraction and total reflection effects.

Said mosaic channel with graded convergence can be contained in a multi layer casing to avoid the dispersions of not collimated neutrons radiations and/or parasitic gamma radiations or other. This casing, indicated with 32 in FIG. 3(c), will be made by foils and interspace (e.g. Pb, Cr, $H_2O$, $B_4C$ and other can be used for the material of foils and the interspace filling) indicated by 32 in FIG. 3(c).

For example, considering a combination $H_2O$, $D_2O$ and other, it's possible to obtain at the exit of the extraction channel the 25% of neutrons captured by the central channel. The minor deviations from the axial direction of the neutron motion can be compensated by the graded curvature of the central and extraction channels. A design, achievable trough a Monte Carlo simulation, leads to use a suitable combination of $D_2O$, water, Plexiglass and others materials to obtain the appropriate convergence and thermalization of at least 0.1% of the neutrons emitted from the source. This is the minimum ToReRe lens efficiency. With the source specification adopted as an example, the mentioned efficiency provides a neutrons flux ranging between $10^5$-$10^7$ neutron per sec per square centimetre. The dimension of the lens is contained in square cubic meter.

The Detector

The neutrons detector is preferable made of a $^3$He gas counter; that shows high cross section and good marketability with the additional advantage to use low voltage generator. An array of detectors and related enabling detection controllers can be used in combination of electronic filters and monocromators.

Figure 4:
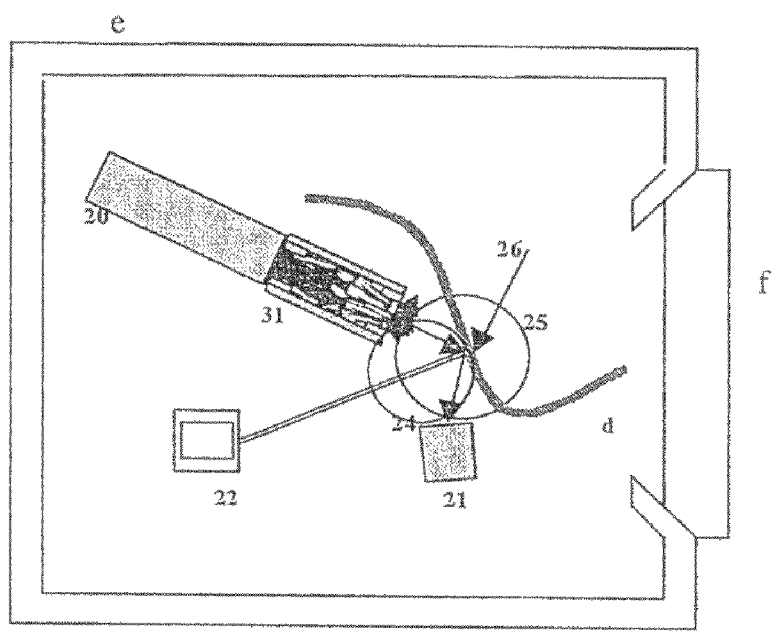
FIG. 4 shows schematically an apparatus according to the invention

FIG. 4 shows a scheme of a possible realization of the invention in which it is possible to see: the neutrons generator (source) 20, the irradiating lens 31, the detector 21, the virtual goniometer circle 25, the focusing circle 24, the centring window 22 and its projections in the centre of the virtual goniometer 26.

In FIG. 4, the plane where the robots are set and move the source 20, the centring window 22, and the detector 21, can be movable and corresponds to the plane 13 (see FIG. 1). The wall "e" and "f" are for confinement of the measure area and can eventually be filled with water with a suitable concentration of Boron (for the capture of neutrons) and Carbon (for the capture of gamma (γ) rays). The wall "e" can be mobile or tilting to favor the positioning of the platform that support all the equipment respect to the analyzed object; even the wall (I) can be removable to favor the operation of adjustment of the device and the positioning for capturing possibly disperse radiation.

For the sake of completeness the figure shows also the object to be analysed that is indicated by (d).

The application of a robotized device according to the present invention offers the opportunity of linking observation methods to measure and the repairs of damages (diagnosis and therapies) in a "combined and multiple way". For example, using the "radiation-detection" system together with the pointing system "laser-camera-centring window", said combination allows to use a unique device to realize in a not destructive way different diagnostic and therapeutic exercises. This "combined and multiple" use allows such device to be used for diagnostic purposes, hitch and/or damage repair (therapeutic) and eventually even to verify the quality of the repair in course. For example in case of a use of high power X ray it's possible to reduce slits (or damages) on composed materials caused by mechanical stress effect. The virtual goniometer configuration allows to individuate the best crystallographic directions for the repairs and then (or even at the same time) observe the repair effect using different radiation sources. It's possible to use also optical laser sources and even sources that cover different ranges of the electromagnetic spectrum; it is possible to use also a combination of acoustics radiation (acoustic, ultracoustic or subacoustics) or radiations of either charged or neutrals particles. It's possible to employ diffractometric, spectroscopic, lithographic and others techniques. With the same principle it's possible also to induce a controlled alteration of the structure of the material and use them with a purpose of branding and/or labelling.

Moreover the device offers the possibility of being moved using vehicles of common usage (with evident advantage and possibility of multiple use).

When neutrons sources, high power x ray, electrons or other damaging radiations are used, a suitable shield has to be provided. In case of x ray, electrons and neutrons, the use of lenses allows the reduction of particle spread in the solid angle and favours the choice of confining walls based on materials already available.

The invention claimed is:

1. A mobile robotic apparatus comprising:
a source for radiating a specimen, wherein said apparatus is configured to move along a controlled trajectory to observe, from different positions, radiation emitted from an irradiated area of the specimen which is either mobile or fixed;
a mobile surface (10), a first shelf (12) and a central shaft (11) coupled therebetween the mobile surface and first shelf, the central shaft being mechanically, electrically or manually movable and configured to move the first shelf (12) vertically along a z-axis with respect to the mobile surface, a second shelf mounted over said first shelf and configured to slidably move horizontally along an x-axis and y-axis with respect to the first shelf (12) by mechanical gears and guides which are controlled manually or electrically; and
three robots (14, 15, 16) including a central robot (15) and two external robots (14, 16) which are arranged to define a mobile virtual goniometer, each said robot being configured to move along a predetermined and controlled trajectory and comprising a base (17) coupled to the second shelf, a lower arm (18) extending from the base, and an upper arm (18') having a proximate end joined through a joint (19) to the lower arm, the joint being configured to rotate the upper arm (18') with respect to the lower arm (18), and the upper arm (18') having a free end opposite to the joint (19), wherein the free end of one of the two external robots supports the source of radiation (20), the free end of the other external robot supports a detector (21), and wherein the free end of the upper arm of the central robot (15) supports a pointing system with a centring window (22).

2. The apparatus according to claim 1 in which said bases (17) of the robots (14,15,16) are provided with electronically controlled trolleys configured to move on the second shelf (13) freely or to slide on suitable rails formed in a surface of the second shelf (13).

3. The apparatus according to claim 1, wherein each base (17) is provided with motors configured to rotate the lower arm (18) around a plane defined by x and y axes, and in which each joint (19) is provided with motors configured to allow the rotation around the x and y axes.

4. The apparatus according to the claim 1, wherein said central robot includes a telescopic arm to extend the centring window (22) towards the specimen without any direct contact.

5. The apparatus according to claim 1, wherein said source (20), detector (21) and the centring window (22) are linked to the respective upper arms (18') through a joint (23) configured to rotate those devices around one or more planes defined by the x-y-z axes.

6. The apparatus according to claim 5, wherein said pointing system includes two optic lasers (LA) and (LB), a CCD camera (TC) and the centring window (22).

7. The apparatus according to claim 1, wherein said source of radiation is a neutron source that is thermalized or partially thermalized.

8. The apparatus according to claim 7, wherein said neutron source is a pulsed source provided with an electronic filter to cut off neutrons with extreme energy values, and radiation lenses to increase beam density of the irradiated area.

9. The apparatus according to claim 1, wherein said detector includes a 3He gas counter.

10. The apparatus according to claim 1 further comprising walls to confine the measurement area; said walls being mobile or tiltable-up or removable to favor the positioning of the platform (13) that supports all the apparatus relatively to the analyzed object.

11. The apparatus according to claim 7, wherein the neutron source is in combination with other radiation sources.

12. The apparatus according to the claim 1, wherein said centring window includes covering material to reveal the radiation.

13. The apparatus according to the claim 1, wherein said centring window (22) further includes means to project and detect at distance lines, masks and frames.

14. The apparatus according to the claim 1, wherein said centring window (22) further includes means for sputtering covering materials on the surface.

15. The apparatus according to claim 1, wherein said detector includes at least one of a monocromator and a detection controller.

* * * * *